United States Patent
Piers et al.

(10) Patent No.: US 6,830,332 B2
(45) Date of Patent: Dec. 14, 2004

(54) OPHTHALMIC LENS

(75) Inventors: Patricia Ann Piers, Groningen (NL); Hendrik Albert Weeber, Groningen (NL)

(73) Assignee: Advanced Medical Optics, Inc., Santa Ana, CA (US)

(*) Notice: Subject to any disclaimer, the term of this patent is extended or adjusted under 35 U.S.C. 154(b) by 56 days.

(21) Appl. No.: 10/119,661

(22) Filed: Apr. 10, 2002

(65) Prior Publication Data

US 2003/0063254 A1 Apr. 3, 2003

Related U.S. Application Data

(60) Provisional application No. 60/285,954, filed on Apr. 24, 2001.

(30) Foreign Application Priority Data

Apr. 11, 2001 (SE) ............................................. 0101293

(51) Int. Cl.$^7$ ............................. G02C 7/02; G02C 7/04; A61F 2/16
(52) U.S. Cl. ................ 351/159; 351/160 R; 351/160 H; 351/177; 623/6.31
(58) Field of Search ......................... 623/6.31; 351/159, 351/160 R, 160 H, 161, 162, 177; 359/558

(56) References Cited

U.S. PATENT DOCUMENTS

| 4,642,112 A | 2/1987 | Freeman |
| 4,655,565 A | 4/1987 | Freeman |
| 5,117,306 A | 5/1992 | Cohen |
| 5,384,606 A | 1/1995 | Koch et al. |
| 5,895,422 A | 4/1999 | Hauber |
| 6,019,472 A | 2/2000 | Koester et al. |
| 6,154,323 A | * 11/2000 | Kamo .......................... 359/691 |
| 6,338,559 B1 | * 1/2002 | Williams et al. ............. 351/212 |

* cited by examiner

Primary Examiner—Scott J. Sugarman
(74) Attorney, Agent, or Firm—Holly Kozlowski; Peter Jon Gluck

(57) ABSTRACT

According to the invention the ophthalmic lens further comprises a refractive part comprising at least one surface, which is configured to compensate a passing wavefront at least partly for at least one type of monochromatic aberration introduced by at least one of the optical parts of the eye. Said diffractive part is capable of compensating a passing wavefront at least partly for chromatic aberration introduced by at least one of the optical parts of the eye. Furthermore said refractive and diffractive parts together contribute to a required power of the lens.

43 Claims, 2 Drawing Sheets

OPHTHALMIC LENS

RELATED APPLICATION

The present application claims priority under 35 U.S.C. §119(e) of U.S. Provisional Application Ser. No. 60/285,954 filed Apr. 24, 2001.

TECHNICAL FIELD OF THE INVENTION

The present invention relates to an ophthalmic lens comprising a diffractive part.

Furthermore it relates to a method for designing said ophthalmic lenses.

BACKGROUND OF THE INVENTION

A wavefront passing the eye will be influenced by the optical parts of the eye such that for example chromatic aberration is provided to the wavefront. The reason is that the refractive indices of the materials in the optical parts of the eye differ for different wavelengths. Thus light having different wavelengths will be refracted a different amount and they will fall on the retina at different places, i.e. different colors can not be focused to the same point. This is called chromatic aberration.

Recently there has been much interest in the correction of the monochromatic aberrations of the eye. It has been revealed that when all monochromatic aberrations are corrected in the human visual system, it serves to unmask the chromatic aberration of the eye. Therefore, in order to optimize the optical quality of the eye, a combination of monochromatic and chromatic aberrations needs to be corrected. A diffractive pattern could be configured to provide a passing wavefront with chromatic aberration of the opposite sign as chromatic aberration from the eye. Thus a diffractive pattern can be used to correct for chromatic aberration introduced to a wavefront from the optical parts of the eye. Some background theory of chromatic aberration can be found in, for example Chapter 17 in "Optics of the Human Eye" written by David A. Atchison and George Smith. A theoretical background of the diffractive pattern could be found in the article "Practical design of a bifocal hologram contact lens or intraocular lens", Allen L. Cohen, Applied Optics 31(19)(1992). Ophthalmic lenses, which on at least one surface comprises a diffractive pattern for correcting for chromatic aberration are known from for example U.S. Pat. Nos. 5,895,422, 5,117,306 and 5,895,422. These lenses do, however not, compensate for other aberrations provided by the eye surfaces. In SE 0001925-7, and WO 01/89424, aspheric lenses are designed to compensate for spherical aberration. In some applications these lenses will provide the eye with an increase in chromatic aberration. It is therefor a need of an ophthalmic lens for correcting refractive errors that also can correct for monochromatic and chromatic aberrations.

DESCRIPTION OF THE INVENTION

An object of the present invention is to improve the visual quality for a patient.

A further object of the present invention is to provide an ophthalmic lens, which corrects for chromatic aberration and at least one type of monochromatic aberration.

A further object of the present invention is to provide an ophthalmic lens, which corrects for both chromatic and spherical aberration.

Still a further object of the invention is to correct for spherical aberration as expressed by the $11^{th}$ normalized Zernike term.

A yet further object is to provide an aspheric lens capable of correcting for spherical aberration having a diffractive part adding refractive power to the lens and providing compensation for chromatic aberration introduced by the optical surfaces of the eye and by the aspheric lens surface. In this text the term aspheric will refer to rotationally symmetric, asymmetric and/or irregular surfaces, i.e. all surfaces differing from a sphere.

These objects are achieved by an ophthalmic lens as initially described in "technical field of invention", which according to the invention further comprises a refractive part comprising at least one surface, which is configured to compensate a passing wavefront at least partly for at least one type of monochromatic aberration introduced by at least one of the optical parts of the eye. The diffractive part is according to the invention capable of compensating a passing wavefront at least partly for chromatic aberration introduced by at least one of the optical parts of the eye. Said refractive and diffractive parts together contribute to a required power of the lens. In this text "the optical parts of the eye" refer to the parts of the eye that contribute to the refraction of incoming light. The cornea of the eye and the natural or an implanted lens are optical parts of the eye. But also inhomogeneities, e.g. in the vitreous are considered as the optical parts of the eye. An optical element that combines both diffractive and refractive optics is called a hybrid element. The monochromatic aberration could be for example astigmatism, coma, spherical aberration, trifoil, tetrafoil or higher aberration terms.

Hereby an ophthalmic lens is achieved that is capable of compensating for at least one type of monochromatic aberration and for chromatic aberration introduced by the optical parts of the eye to a passing wavefront.

Preferably the diffractive part also is capable of compensating a passing wavefront at least partly for chromatic aberration introduced by the refractive part of the lens.

In one embodiment of the invention the monochromatic aberration corrected for is spherical aberration.

The longitudinal chromatic aberration of the eye is very well understood and has been shown to have very similar values from subject to subject (Thibos et. al., "The chromatic eye: a new reduced heye model of ocular chromatic aberration in humans", Applied Optic, 31, 3594–3600, (1992)). It has also been shown to be stable with age (Mordi et. al., "Influence of age on chromatic aberration of the human eye", Amer. J. Optom. Physiol. Opt., 62, 864–869 (1985)). Hereby an ophthalmic lens to correct for the average chromatic aberration of the eye could be designed.

Diffractive surfaces can be characterised by their so called phase functions. This phase function describes the additional phase that is added to a ray when it passes the diffractive surface. This additional phase is dependent on the radius of the lens where the ray strikes the surface. For radially symmetric diffractive surfaces this function can be described using Equation 1.

$$\phi(r) = \frac{2\pi}{\lambda}(DF0 + DF1r + DF2r^2 + DF3r^3 + DF4r^4 + \ldots) \quad (1)$$

Where r is the radial coordinate, $\lambda$ the wavelength and DF0, DF1 etc. are the coefficients of the polynomial.

The diffractive part of the lens can also introduce some spherical aberration to a passing wavefront. Preferably, according to the present invention, the refractive part is made capable to compensate a passing wavefront for the spherical aberration introduced by the diffractive part of the lens. Hereby, the spherical aberration could be reduced to a minimum after the wavefront has passed the optical parts of the eye and said lens.

To compensate for the spherical aberration, an aspherical surface, with a lateral height described by Equation 2, could be introduced to the refractive part of the lens. An aspheric surface can be configured to counteract the spherical aberration introduced by the optical parts of the eye and by the diffractive part of the lens. All the optical parts of the eye do not necessarily have to be considered. In one embodiment it is sufficient to measure the spherical aberration introduced by the cornea of the eye and compensate for only the spherical aberration provided by the cornea and optionally also for the spherical aberration introduced by the diffractive part of the lens. For example Zernike terms could be used to describe the optical surfaces of the eye and thus also be used to configure the aspheric surface of the lens, which is adapted to compensate for the spherical aberration. Table 1 shows the first 15 normalized Zernike terms and the aberrations each term signifies. The spherical aberration is the $11^{th}$ normalized Zernike term. The designing of a lens that is adapted to compensate for aberrations as expressed in Zernike terms is explained in further detail in the Swedish patent application SE 0000614-4 to which is given reference.

$$z = \frac{\left(\frac{1}{R}\right)*r^2}{1+\sqrt{1-\left(\frac{1}{R}\right)^2(cc+1)r^2}} + ADr^4 + AEr^6 \quad (2)$$

Where R is the radal coordinate of the lens, cc is the conic constant, and AD and AE are coefficients of the polynomial extension.

TABLE 1

| i | $Z_i$ (ρ,θ) (normalized format) | form associated with normalized polynomial |
|---|---|---|
| 1 | 1 | Piston |
| 2 | 2ρcos θ | Tilt x |
| 3 | 2ρsinθ | Tilt y |
| 4 | √3(2ρ² − 1) | Defocus |
| 5 | √6(ρ² sin 2θ) | Astigmatism $1^{st}$ order (45°) |
| 6 | √6(ρ² cos2θ) | Astigmatism $1^{st}$ order (0°) |
| 7 | √8(3ρ³ − 2ρ)sin θ | Coma y |
| 8 | √8(3ρ³ − 2ρ)cos θ | Coma x |
| 9 | √8(ρ³ sin 3θ) | Trifoil 30° |
| 10 | √8(ρ³ cos 3θ) | Trifoil 0° |
| 11 | √5(6ρ⁴ − 6ρ² + 1) | spherical aberration |
| 12 | √10(4ρ⁴ − 3ρ²)cos 2θ | Astigmatism $2^{nd}$ order (0°) |
| 13 | √10(4ρ⁴ − 3ρ²)sin 2θ | Astigmatism $2^{nd}$ order (45°) |
| 14 | √10(ρ⁴ cos 4θ) | Tetrafoil 0° |
| 15 | √10(ρ⁴ sin 4θ) | Tetrafoil 22.5° |

The spherical aberration of the lens is influenced by the shape factor of the lens. The spherical aberration of a spherical refractive lens can be minimized by a convex-plano lens (Atchison D. A., "Optical Design of Intraocular lenses. I: On-axis Performance", Optometry and Vision Science, 66 (8), 492–506, (1989)). In the present invention, the amount of correction of spherical aberration depends on the shape factor of the lens. It is also possible to use a diffractive pattern that is able to correct for spherical aberration as well as for chromatic aberration. This can be done by modifying the higher orders of the phase function of the diffractive profile (lower orders, or terms on $r^2$ (Equation 1), describe the paraxial properties of the lens).

Other types of monochromatic aberrations can also be corrected for by aspheric refractive surfaces. The shape of the surface becomes more complex the higher the order of the aberration that is corrected. To compensate for a general aberration with an aspherical surface, the lateral height could be described by Equation 3, though also other descriptions are possible.

$$z = \sum_{i=1}^{n} z_i$$

$z_i = (asi)x^j y^k$ $i = \frac{1}{2}[(j+k)^2 + j + 3k]$

Where asi are the coefficients of the polynomial.

Preferably the ophthalmic lens together with the eye provides a polychromatic image quality, which when expressed as MTF(50) (Modulation Transfer Function at 50 cycles per millimeter) performs at least about 40% higher than an aspheric lens compensating for the same spherical aberration as the inventive lens but without compensating for the chromatic aberration. A high value of the polychromatic image quality indicates that the amount of chromatic aberration is small and also that the amount of monochromatic aberrations is small.

The lens can correct for the spherical aberrations and the chromatic aberrations as defined in a model eye. Spherical aberration of the eye can run between zero and 1.5 diopter, while chromatic aberration typically runs up to 2.5 diopters ("Optics of the Human Eye" written by David A. Atchison and George Smith).

Suitably, the diffractive part is a diffractive surface profile. Such a diffractive surface profile consists of a number of concentric rings. The distances between the rings are decreasing out from the center of the lens. The area between two rings is called a zone. The width of the first zone is a constant that defines the widths of all the other zones. For more background techniques see the article by Allen L. Cohen referred to on page 1 in this application.

In one embodiment, the profile height is equal to one design wavelength. 550 nm is often used as the design wavelength since this is the wavelength for which the retina has its maximum sensitivity. When the profile height is equal to one design wavelength the lens will have its maximum effect in its first order. The profile height is, in another embodiment equal to two design wavelengths and then the lens will have its maximum effect in its second order. See e.g. the aforementioned article by Allen L. Cohen and the U.S. Pat. Nos. 5,895,422, 5,117,306, 5,895,422. The profile height could be any integer number of the design wavelengths.

In one embodiment of the invention the anterior surface of the lens is an aspheric surface, on which a diffractive profile is superimposed. In another embodiment of the invention the anterior surface of the lens is an aspheric surface and the posterior surface of the lens is flat and has a diffractive profile. Also other combinations are possible. For example a diffractive profile could be provided on both the anterior and the posterior surface. Both the anterior and posterior surfaces could also be aspheric. The skilled person can readily identify alternative lens configurations which will be suitable to design the inventive chromatic and monochromatic aberration reducing lenses.

The objects are also achieved by a method as initially described comprising combining a refractive part and a diffractive part of the lens such that they together compensate a passing wavefront at least partly for at least one type of monochromatic aberration and for chromatic aberration introduced by at least one of the optical parts of the eye, while dimensioning said refractive and diffractive parts to provide the lens with a required power.

In one embodiment the method further comprises measuring at least one type of monochromatic aberration provided to a wavefront from at least one of the optical parts of an eye and combining the refractive and diffractive parts of the lens such that they compensate at least partly for the measured monochromatic aberration.

In one embodiment of the invention the measured monochromatic aberration is spherical aberration.

The spherical aberration of the whole eye could be measured using a wavefront sensor. If only the cornea is considered well-known topographical measurement methods could be used. Such topographical methods are disclosed in for example "Corneal wave aberration from videokeratography: accuracy and limitations of the procedure", Antonio Guirao and Pablo Artal, J. Opt. Soc. Am. Opt. Image Sci. Vis., June, 17(6), 955–965, (2000). A wavefront sensor is described in U.S. Pat. No. 5,777,719 (Williams et. al.).

Suitably, the method further comprises measuring the chromatic aberration provided to a wavefront from at least one of the optical parts of the eye and combining the refractive and diffractive parts of the lens such that they together compensate a passing wavefront at least partly for the measured chromatic aberration introduced by at least one of the optical parts of the eye. The chromatic aberration of the eye could be measured by using vernier methods such as those similar to the methods outlined in Thibos et. al., "Theory and measurement of ocular chromatic aberration", Vision Res., 30, 33–49 (1990) and Marcos et. al, Vision Research, 39, 4309–4323, (1999). Alternative ways for measuring chromatic aberration are described in a textbook, "Optics of the Human Eye" by David A. Atchison and George Smith, published by Butterworth-Heinemann, ISBN 0-7506-3775-7.

Preferably, the method further comprises measuring the refractive error of the eye and dimensioning the refractive and diffractive parts of the lens such that they together compensate at least partly for the refractive error of the eye.

With this method of designing an ophthalmic lens the chromatic aberration, the spherical aberration and the refractive error of the eye, could all be considered and compensated for. The lens is designed with one refractive part and one diffractive part and they are combined, such that they together compensate a passing wavefront for these aberrations introduced by the optical parts of the eye.

The aberration corrections could all be full corrections or partial corrections. Furthermore all the corrections could be based on the aberrations of one or more parts of the eye. The corrections could also be based on either an average value of a certain population or on the measured values of the individual patient or on a combination of an average value and individual measurements. The certain population can be a group of people in a specific age interval or for example a group of people having had an eye disease or a corneal surgery. For chromatic aberration the values are pretty much the same for all humans so it is possible to take an average value of all kinds of people and correct for this chromatic aberration in the lens. Of course it is possible to do the same for spherical aberration but in this case it would be preferred to choose a group of people or even measure the spherical aberration for every individual since the spherical aberration will differ more from eye to eye than chromatic aberration.

The ophthalmic lens could be configured to be a phakic or pseudophakic intraocular lens (IOL), a spectacle lens or a contact lens. In the examples described below the lenses are pseudophakic IOLs. The material used in the example lenses described below is a foldable silicone high refractive index material described in U.S. Pat. No. 5,444,106. Other materials are however also possible for these lenses. For example PMMA (Poly-methylmethacrylaat) and hydrogels are suitable materials. The example lenses have a power of 20D. However, the lenses could be designed to have any other suitable power. Also negative lenses are possible.

A method of designing the ophthalmic lens described above comprises the steps of:

i) selecting an eye model with a refractive aspheric ophthalmic lens of a predetermined refractive power and a predetermined amount of at least one monochromatic aberration;

ii) estimating the power of said eye model at different wavelengths, so as to determine the chromatic aberration of the eye model;

iii) estimating a correction function of how the power varies with the wavelength to be an ideal compensation for said chromatic aberration of the eye model;

iv) finding a linear function of how power varies with the wavelength, which suitably approximates said correction function;

v) calculating a provisional zone width of a diffractive profile corresponding to this linear function and also calculating the diffractive power of this diffractive profile;

vi) reducing the refractive power of the refractive ophthalmic lens by the amount of power calculated for the diffractive profile;

vii) estimating a new correction function of step iii), finding a new linear function of step iv) and calculating a new provisional zone width and a new diffractive power for a new diffractive profile corresponding to this new linear function;

viii) adjusting the refractive power of the refractive ophthalmic lens such that the total power of a hybrid lens, which comprises both the refractive ophthalmic lens and the diffractive profile and which is adapted to replace the refractive ophthalmic lens in the eye model, equals the predetermined power;

ix) repeating steps vii) to viii) until a suitable combination of a refractive and a diffractive part of the hybrid ophthalmic lens is found that both provide the eye model with a predetermined power and with a suitable reduction in chromatic aberration.

Suitably this method comprises as a last step measuring the monochromatic aberration of the combination of the eye and the hybrid ophthalmic lens of the method above and correcting the refractive part of the ophthalmic lens according to the measurements such that the monochromatic aberration is reduced sufficiently for the combination of eye and ophthalmic lens.

One example of an eye model that can be used is the eye model of Navarro but other models are also possible. The eye model could also be an individual eye of an individual patient.

In one embodiment the at least one monochromatic aberration of the refractive ophthalmic lens is spherical aberration.

There are different possibilities for the design of the lenses according to the invention. One possibility is to design each lens for each individual. Then the chromatic aberration, the spherical aberration and the refractive error of the eye of the patient are measured and a lens is designed from these values according to the above described method. Another possibility is to use average values from selected categories of people to design lenses adapted to suit almost all the people belonging to this category. It would then be possible to design lenses having different powers but providing the same reduction of spherical and chromatic aberration to patients within these groups of people. The groups of people could for example be age groups or groups of people having had specific eye diseases or a group of people having had a corneal surgery. Furthermore it would be possible to provide a kit of lenses having an average value of chromatic aberration and a range of different values of spherical aberration for each power. This could be preferred since the chromatic aberration is about the same in most human eyes. Hereby it would be necessary to measure the refractive error and the spherical aberration of each individual eye and then choose one lens from this kit of lenses to comply with these measurements.

The following examples are just given as examples and are not intended to be limiting for the invention in any way.

BRIEF DECRIPTION OF DRAWINGS

DETAILED DESCRIPTION OF EMBODIMENTS

Two examples are described of an intraocular lens (IOL) which corrects for spherical aberration and for chromatic aberration of the pseudophakic eye. Both examples use an aspheric lens surface for correcting the spherical aberration and a diffractive surface profile for correcting the chromatic aberration. The aspheric lens surface corrects the spherical aberration of the ocular surfaces, as well as the spherical aberration induced by the diffractive lens profile.

Example 2 has an extended diffractive surface profile. This type of lens is often called a super-zone diffractive lens and such lenses are described in: J. C. Marron et al., "Higher-Order Kinoforms", Computer and optically formed holographic optics, I. Cindrich, et al., editor, Proc. SPIE 1211, 62–66 (1990).

The configuration of the example IOLs is fully described below, based on an eyemodel taken from the literature (Navarro et al, "Accommodation dependent model of the human eye with aspherics." JOSA A, 2(8), 1273–1281, (1985)) and based on the data of a silicone material. The optical evaluation is done by ray tracing using the OSLO optical design software (Lambda Research Corporation, Littleton, Mass., USA).

EXAMPLE 1

Background Theory:

Both the cornea and the refractive intraocular lens (IOL) have a positive chromatic aberration, which means that the focal length increases with longer wavelength. A diffractive profile has a negative chromatic aberration. The profile consists of a number of rings (zones). For a diffractive lens working in the $1^{st}$ diffraction order, the power of lens can be defined by:

$$P = \frac{2*\lambda}{w^2}$$

Where P is the lens power, λ is the design wavelength (m) and w is the Half-width (radius) of the first zone.

The chromatic aberration (CA) can be described as:

$$CA = -\frac{\partial P}{\partial \lambda} = -\frac{2}{w^2}$$

Figure 1:
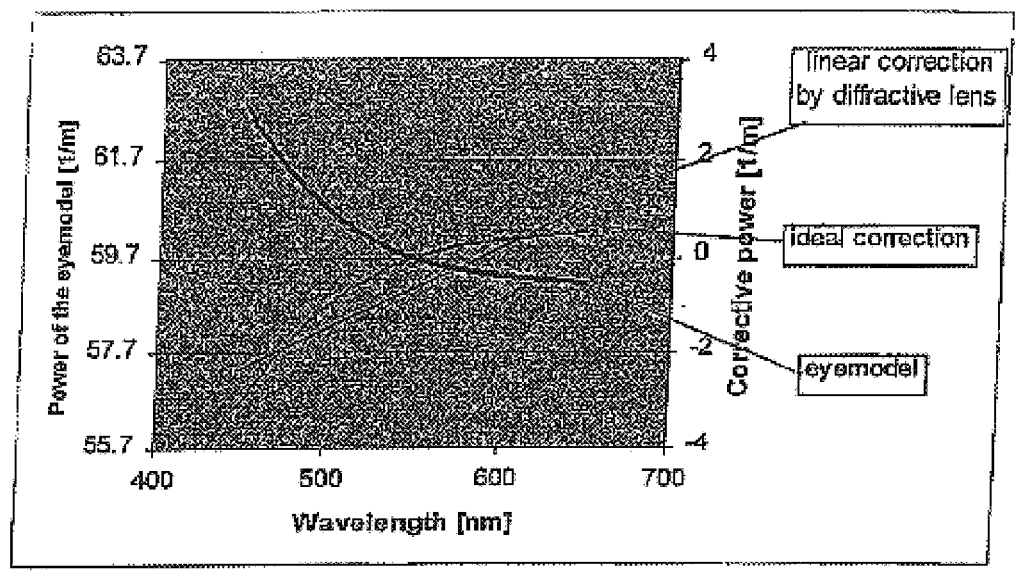
FIG. 1 shows a diagram of the relationship between refractive power and wavelength for an eyemodel and for a diffractive lens.

The diffractive lens power is linearly related to the wavelength. The relation between refractive lens power and wavelength, in refractive systems, is generally not linear. This is shown in FIG. 1 where the relation between refractive power and wavelength for an eyemodel and for a diffractive lens is illustrated. The eyemodel has a non-linear relationship and the diffractive lens has a linear relationship. A curve, representative for an ideal correction is also shown. Therefore, a perfect correction cannot be made with a diffractive lens. Nevertheless, with a linear correction, the optical performance can be greatly improved.

When the eyemodel of Navarro (1985) is used, together with a 20 diopter silicone refractive intraocular lens instead of the natural lens, the chromatic aberration can be estimated by calculating the power of the eyemodel at different wavelengths. A graph similar to FIG. 1 will be the result. In order to determine how the diffractive lens must perform, a linear fit is made through the curve of the ideal correction. The result is:

$$P = -1.68 \cdot 10^7 * \lambda + 69.6$$

P=power [1/m]
λ=wavelength [m]

This gives the ratio between the refractive and diffractive IOL power for a chromatic correction lens:

For the eyemodel with a refractive IOL:

$$CA = -\frac{\partial P}{\partial \lambda} = 1.68 \cdot 10^7$$

So:

$$\frac{2}{w^2} = -1.68 \cdot 10^7 \Rightarrow w = 0.345 \text{ mm} \Rightarrow P_d = \frac{2\lambda}{w^2} = 9.24 \text{ diopter}$$

(here, λ is the design wavelength of 550 nm) $P_d$=IOL diffractive power

Since the diffractive IOL power is 9.24 diopter, the refractive IOL power has to be reduced by the same amount. Reducing the refractive IOL power will reduce the chromatic aberration of the eyemodel also. In practice, equilibrium has to be found between the refractive and diffractive IOL power by an iterative design process, where the diffractive IOL power will end up somewhere between 0 and 9.24 diopter.

Description of the Lens:

The example lens is made of silicone material. Its shape is equi-biconvex. The anterior surface of the lens comprises an aspheric refractive lens, on which a diffractive profile is superimposed. The diffractive profile takes care of 41% (8.25D) of the lens power, while the aspheric refractive lens does the remaining 59% (11.75D). The width of the first zone is 0.365 mm, and there are 67 rings needed to fill a full 6.0 mm IOL optic. In the periphery of the lens, the diffractive rings are 22 microns apart from each other.

The IOL is optimized for the Navarro (1985) eyemodel. The Navarro eyemodel has an aspheric cornea and includes dispersion for the ocular media. The surface information for the eye model and the lens is given in table 2. The lens designed is dependent on the eye model chosen. It must be noted that it is possible to design lenses using other eye models of actual physiological data from patients.

cycles/mm. The polychromatic MTF is determined by the weighed average of the 4 MTF's at the 4 wavelengths used. The weighting of the wavelengths was done using the standard luminance of the eye under photopic light conditions, which represents the relative sensitivity of the retina for different wavelengths. The actual back focal length (ABFL) for the 4 different wavelengths indicates the presence of a chromatic difference in focus and by definition the amount of longitudinal chromatic aberration. The calculations are performed at a 5.0 mm aperture in order to maximize the differences. From these figures, shown in table 3, it can already be concluded that the spherical aberration is virtually eliminated, indicated by the close to diffraction

TABLE 2

*LENS SURFACE DATA - Navarro 1985 with an IOL

| Surface | Radius | Thickness | Aperture Radius | Glass | Special surface |
|---|---|---|---|---|---|
| Object | — | 1.0000e + 20 | 1.000e + 14 | AIR | |
| 1 | 7.7200 | 0.5500 | 2.833 (solved) | CORNEA | Asphere |
| 2 | 6.5000 | 3.050 | 2.778 (solved) | AQUEOUS | |
| 3 (pupil) | — | — | 2.500 (solved) | PUPIL | |
| 4 | — | 0.900 | 2.500 (solved) | AQUEOUS | |
| 5 | 20.994 | 1.125 | 2.418 (solved) | SILICONE | Asphere Diffractive |
| 6 | −20.994 | 18.157 (solved) | 2.298 (solved) | VITREOUS | |
| Image | — | — | 1.674e − 05 (solved) | — | |

CONIC AND POLYNOMIAL ASPHERIC DATA

| Surface | conic constant | AD | AE |
|---|---|---|---|
| 1 | −0.260000 | — | — |
| 5 | −2.000000 | −0.000459 | 4.1000e − 07 |

*DIFFRACTIVE SURFACE DATA (symmetric diffractive surface)

| Surface | Diffraction order | Design λ | Kinoform construction order | Kinoform zone depth | DF0 | DF1 |
|---|---|---|---|---|---|---|
| 5 | 1 | 0.550 μm | 1 | — | — | −0.004125 |

*WAVELENGTHS

| λ number | Wavelength (μm) | Weight |
|---|---|---|
| 1 | 0.5500 | 0.9950 |
| 2 | 0.4500 | 0.0380 |
| 3 | 0.6500 | 0.1070 |
| 4 | 0.5100 | 0.5030 |

*REFRACTIVE INDICES

| Surface | Name | Index λ (1) | Index λ (2) | Index λ (3) | Index λ (4) | v |
|---|---|---|---|---|---|---|
| Object | AIR | 1.000000 | 1.000000 | 1.000000 | 1.000000 | — |
| 1 | CORNEA | 1.377400 | 1.383500 | 1.374200 | 1.379328 | 40.580645 |
| 2 | AQUEOUS | 1.338800 | 1.345100 | 1.335600 | 1.340767 | 35.663158 |
| 3 | PUPIL | 1.338800 | 1.345100 | 1.335600 | 1.340767 | 35.663158 |
| 4 | AQUEOUS | 1.338800 | 1.345100 | 1.335600 | 1.340767 | 35.663158 |
| 5 | SILICONE | 1.459620 | 1.484950 | 1.454470 | 1.465680 | 15.079396 |
| 6 | VITREOUS | 1.337400 | 1.343400 | 1.334300 | 1.339286 | 37.076923 |
| Image | IMAGE | — | — | — | — | — |

Behavior of the Lens 4 discrete wavelengths were used to evaluate the eyemodel including the refractive/diffractive IOL. The focus point is defined as the point where the polychromatic MTF (Modulation Transfer Function) has it's maximum at 50 cycles/mm. The polychromatic MTF is determined by the limited performance. The IOL is optimized for chromatic aberration, but there is still some left, as already expected theoretically.

The figures in table 4, for a corresponding aspheric refractive design, without chromatic correction, show that indeed at each wavelength, the spherical aberration is well corrected with respect to the MTF(50) for the spherical refractive IOL and the MTF reaches the diffraction limit. The focal points of the different wavelengths do not work well together, so that the polychromatic MTF is lower than that found for the diffractive/refractive IOL.

Spherical lenses, which are now current practice, give much lower values. The figures corresponding to these lenses are shown in table 5.

TABLE 3

Refractive/diffractive IOL:

| λ | ABFL | MTF(50) | Diff.limit |
|---|------|---------|------------|
| 450 | 17.92 | 0.91 | 0.92 |
| 510 | 18.17 | 0.90 | 0.90 |
| 550 | 18.16 | 0.90 | 0.90 |
| 650 | 17.90 | 0.88 | 0.88 |
| poly | 18.16 | 0.82 | 0.90 |
| [nm] | [mm] | [-] | [-] |

TABLE 4

Aspherical refractive IOL:

| λ | ABFL | MTF(50) | Diff.limit |
|---|------|---------|------------|
| 450 | 17.26 | 0.92 | 0.92 |
| 510 | 17.98 | 0.90 | 0.91 |
| 550 | 18.22 | 0.90 | 0.90 |
| 650 | 18.41 | 0.88 | 0.88 |
| poly | 18.22 | 0.56 | 0.90 |
| [nm] | [mm] | [-] | [-] |

TABLE 5

Spherical refractive IOL:

| λ | ABFL | MTF(50) | Diff.limit |
|---|------|---------|------------|
| 450 | 17.13 | 0.30 | 0.92 |
| 510 | 17.84 | 0.30 | 0.91 |
| 550 | 18.06 | 0.31 | 0.90 |
| 650 | 18.15 | 0.32 | 0.88 |
| poly | 18.05 | 0.21 | 0.90 |
| [nm] | [mm] | [-] | [-] |

Figure 2:
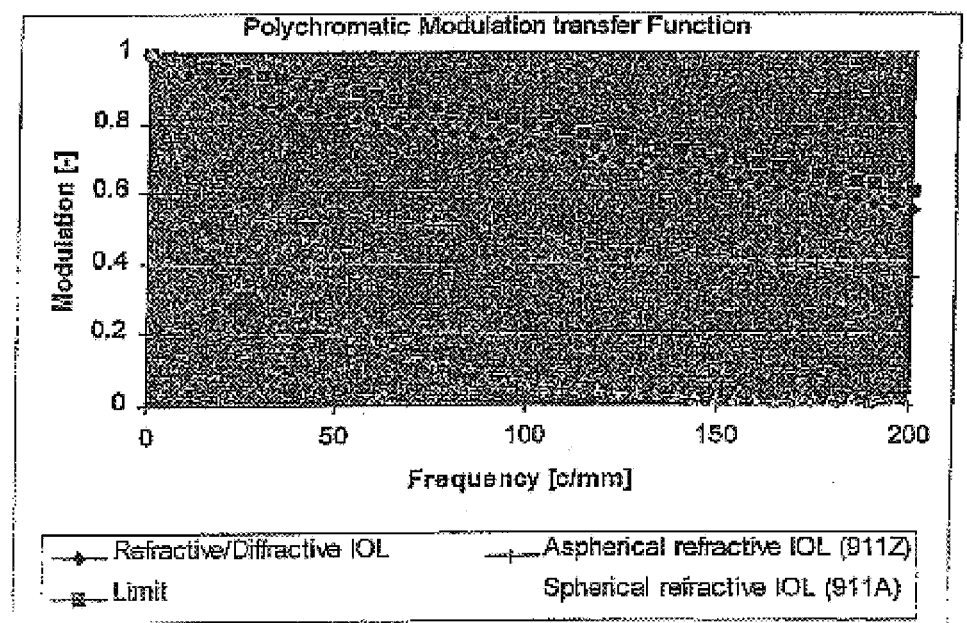
FIG. 2 shows the Polychromatic Modulation Transfer Function for a hybrid refractive/diffractive lens and two other lenses.

The Polychromatic Modulation Transfer Functions for these three lenses are shown in FIG. 2, together with the diffraction limit.

EXAMPLE 2

Background Theory

If a lens, which has fewer rings and thus also larger distances between the rings is preferred, for example for manufacturing reasons, a different step height for the diffractive profile could be used. A diffractive lens that is on the market, CeeOn™ 811E, Pharmacia has a 4D diffractive part, a zone width of 0.5 mm and 32 rings.

A 8.25D diffractive lens with the same spacings between the rings as the existing 811E can be achieved by doubling the step height of the rings. With a double stepheight, the diffractive lens will have a phase jump of 2λ, and therefore give its maximum efficiency in its $2^{nd}$ order. For an 8.25D lens, the zone width will be 0.516 mm while 33 rings will be needed for a 6mm optic. The minimum distance between the rings (periphery) is 45 microns.

Figure 3:
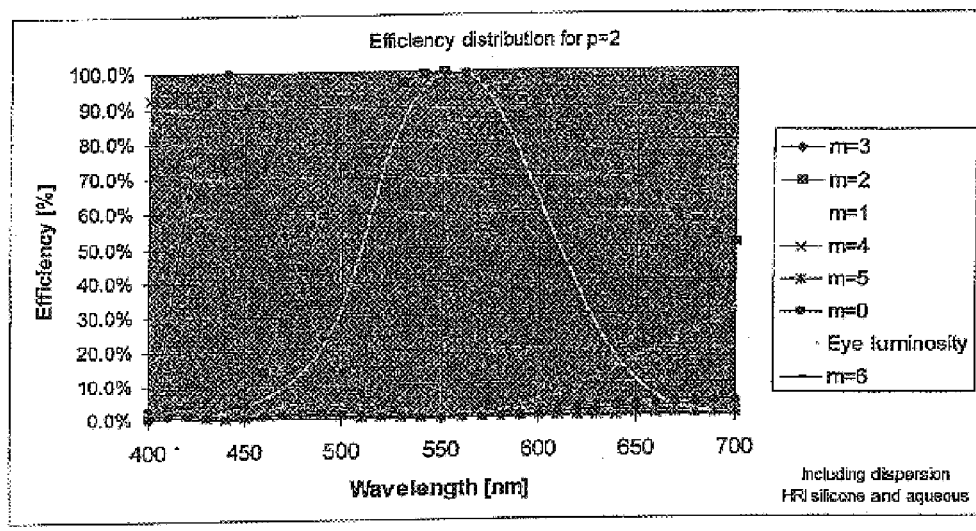
FIG. 3 shows the light distribution between the different diffractive orders for a diffractive lens with a profile height of two design wavelengths. Also shown in this plot is the spectral sensitivity of the eye.

The example lens is made of silicone material. Its shape is convex-plano. The anterior surface of the lens is aspheric. The flat posterior surface has a diffractive profile with a phase jump of two. The light distribution between the different diffractive orders is given in FIG. 3. From this graph we see that only order 1 to 3 are relevant in the visible light range. We also see that there is some bifocal behavior at 475 nm, but the eye is very insensitive to light at this wavelength (as indicated by the eye's spectral sensitivity, also shown in FIG. 3.

Description of the Lens

As in example 1, the diffractive profile takes care of 41% (8.25D) of the lens power, while the aspheric refractive lens does the remaining 59% (11.75D).

The IOL is optimized for the Navarro (1985) eyemodel. The Navarro eyemodel has an aspheric cornea and includes dispersion for the ocular media. The surface information for the eye model and the lens is given in table 6.

TABLE 6

*LENS DATA - Navarro 1985 with an IOL.

| Surface | Radius | Thickness | Aperture Radius | Glass | Special surface |
|---------|--------|-----------|-----------------|-------|-----------------|
| Object | — | 1.0000e + 20 | 1.000e + 14 | AIR | |
| 1 | 7.7200 | 0.5500 | 2.833 (solved) | CORNEA | Asphere |
| 2 | 6.5000 | 3.050 | 2.778 (solved) | AQUEOUS | |
| 3 (pupil) | — | — | 2.500 (solved) | PUPIL | |
| 4 | — | 0.900 | 2.500 (solved) | AQUEOUS | |
| 5 | 10.521 | 1.125 | 2.418 (solved) | SILICONE | Asphere |
| 6 | — | — | 2.302 (solved) | AQUEOUS | Diffractive *2 |
| 7 | −20.994 | 18.256 | 2.302 (solved) | VITREOUS | |
| image | — | — | 0.001279 (solved) | — | |

*CONIC AND POLYNOMIAL ASPHERIC DATA

| Surface | Conic constant | AD | AE |

TABLE 6-continued

| | | | | |
|---|---|---|---|---|
| 1 | −0.260000 | — | — | |
| 5 | −4.900000 | — | — | |

*DIFFRACTIVE SURFACE DATA

| Surface | Diffraction order | Design λ | Kinoform construction order | Kinoform zone depth | DFO | DF1 |
|---|---|---|---|---|---|---|
| 6 | 1 | 0.550 μm | 1 | — | — | −0.002063 |

*WAVELENGTHS

| λ number | Wavelength (μm) | Weight |
|---|---|---|
| 1 | 0.5500 | 0.9950 |
| 2 | 0.4500 | 0.0380 |
| 3 | 0.6500 | 0.1070 |
| 4 | 0.5100 | 0.5030 |

*REFRACTIVE INDICES

| Surface | Name | Index λ (1) | Index λ (2) | Index λ (3) | Index λ (4) | v |
|---|---|---|---|---|---|---|
| Object | AIR | 1.000000 | 1.000000 | 1.000000 | 1.000000 | — |
| 1 | CORNEA | 1.377400 | 1.383500 | 1.374200 | 1.379328 | 40.580645 |
| 2 | AQUEOUS | 1.338800 | 1.345100 | 1.335600 | 1.340767 | 35.663158 |
| 3 | PUPIL | 1.338800 | 1.345100 | 1.335600 | 1.340767 | 35.663158 |
| 4 | AQUEOUS | 1.338800 | 1.345100 | 1.335600 | 1.340767 | 35.663158 |
| 5 | SILICONE | 1.459620 | 1.484950 | 1.454470 | 1.465680 | 15.079396 |
| 6 | AQUEOUS | 1.338800 | 1.345100 | 1.335600 | 1.340767 | 35.663158 |
| 7 | VITREOUS | 1.337400 | 1.343400 | 1.334300 | 1.339286 | 37.076923 |
| Image | IMAGE | — | — | — | — | — |

Behavior of the Lens:

Using the same wavelengths as in example 1 and ignoring the changes in efficiency of the diffractive lens, the polychromatic modulation at 50c/mm is 0.81 (limit=0.90), which is similar to the lens in example 1. If also the $1^{st}$ and $3^{rd}$ orders of the diffractive lens are included in the calculation, taking their corresponding efficiencies into account, the polychromatic modulation at 50c/mm is 0.79.

Figure 4:
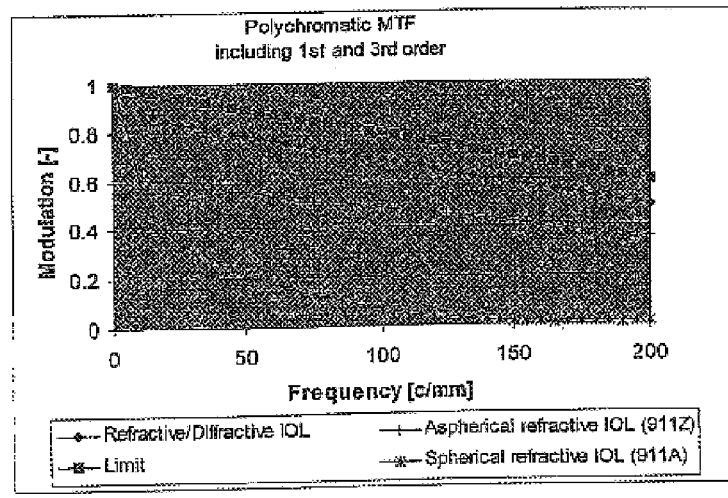
FIG. 4 shows the polychromatic Modulation Transfer Function including $1^{st}$ and $3^{rd}$ order for the lens of FIG. 3 and for two other non-diffractive lenses.

The polychromatic MTF including $1^{st}$ and $3^{rd}$ order for the different lenses are shown in FIG. 4.

What is claimed is:

1. An ophthalmic lens comprising a diffractive part comprising a diffractive surface profile and a refractive part comprising at least one surface, which is configured to compensate a passing wavefront at least partly for at least one type of monochromatic aberration introduced by at least one optical part of the eye, said diffractive part being capable of compensating a passing wavefront at least partly for chromatic aberration introduced by at least one optical part of the eye, said refractive and diffractive parts being adapted together to contribute to a required power of the lens.

2. An ophthalmic lens according to claim 1, wherein the diffractive part is capable of compensating a passing wavefront at least partly for chromatic aberration introduced by the refractive part of the lens.

3. An ophthalmic lens according to claim 1, wherein the refractive part is capable of compensating a passing wavefront at least partly for at least one type of monochromatic aberration introduced by the diffractive part of the lens.

4. An ophthalmic lens according to claim 1, wherein said lens is adapted to compensate at least partly for values of monochromatic and chromatic aberrations measured in the eye of an individual patient.

5. An ophthalmic lens according to claim 1, wherein said lens is adapted to compensate at least partly for an average value of monochromatic and/or chromatic aberration determined by measurements of a group of people.

6. An ophthalmic lens according to claim 1, wherein said refractive part comprises at least one surface, which is configured to compensate a passing wavefront at least partly for spherical aberration introduced by at least one optical part of the eye and optionally also by the diffractive part of the lens.

7. An ophthalmic lens according to claim 1, wherein the refractive part comprises an aspheric surface, which compensates a passing wavefront at least partly for the spherical aberration introduced by at least one optical part of the eye and optionally also by the diffractive part of the lens.

8. An ophthalmic lens according to claim 1, wherein said aspheric surface is capable of compensating at least partly for spherical aberration as expressed by the 11th normalized Zernike term.

9. An ophthalmic lens according to claim 1, wherein the diffractive surface profile consists of a number of concentric rings.

10. An ophthalmic lens according to claim 9, wherein the profile height of the diffractive surface profile equals an integer number of the design wavelength.

11. An ophthalmic lens according to claim 9, wherein the profile height of the diffractive surface profile is one design wavelength.

12. An ophthalmic lens according to claim 1, wherein the lens comprises an anterior surface, and the anterior surface is an aspheric surface, on which a diffractive profile is superimposed.

13. An ophthalmic lens according to claim 9, wherein the profile height of the diffractive surface profile is two design wavelengths.

14. An ophthalmic lens according to claim 1, wherein the lens comprises an anterior surface and a posterior surface, the anterior surface of the lens is an aspheric surface and the posterior surface of the lens is flat and has a diffractive profile.

15. An ophthalmic lens according to claim 1, wherein the shape of the lens is equi-biconvex.

16. An ophthalmic lens according to claim 1, wherein the shape of the lens is convex-plano.

17. An ophthalmic lens according to claim 1, wherein the lens material is a silicone.

18. An ophthalmic lens according to claim 1, wherein the lens material is PMMA or a hydrogel.

19. A method for designing an ophthalmic lens according to claim 1, comprising:

combining a refractive part and a diffractive part of the lens such that they are adapted to together compensate a passing wavefront at least partly for at least one type of monochromatic aberration and for chromatic aberration introduced by at least one optical part of the eye, while dimensioning said refractive and diffractive parts to provide the lens with a required power.

20. A method according to claim 19, further comprising the steps of:

measuring at least one type of monochromatic aberration provided to a wavefront from at least one optical part of an eye; and combining the refractive and diffractive parts of the lens such that they are adapted to compensate at least partly for the measured monochromatic aberration.

21. A method for designing an ophthalmic lens according to claim 19, further comprising the steps of:

measuring the spherical aberration provided to a wavefront from at least one optical part of an eye; and combining the refractive part and the diffractive part of the lens such that they are adapted to together compensate a passing wavefront at least partly for the measured spherical aberration introduced by at least one optical part of the eye.

22. A method according to claim 19, comprising measuring the chromatic aberration provided to a wavefront from at least one optical part of the eye and combining the refractive and diffractive parts of the lens such that they are adapted together to compensate a passing wavefront at least partly for the measured chromatic aberration introduced by at least one optical part of the eye.

23. A method according to claim 19, comprising combining the refractive and diffractive parts of the lens such that they together are adapted to compensate a passing wavefront at least partly for an average chromatic aberration of human eyes in general or of eyes in a specific group of people.

24. A method according to claim 19, comprising combining the refractive and the diffractive parts of the lens such that they together are adapted to compensate a passing wavefront at least partly for an average monochromatic aberration of eyes in general or of eyes in a specific group of people.

25. A method according to claim 19, comprising combining the refractive and diffractive parts of the lens such that the diffractive part is adapted to compensate a passing wavefront at least partly for the chromatic aberration introduced by the refractive part of the lens.

26. A method according to claim 19, comprising combining the refractive and the diffractive parts of the lens such that the refractive part is adapted to compensate a passing wavefront at least partly for the monochromatic aberration introduced by the diffractive part of the lens.

27. A method according to claim 19, comprising measuring the refractive error of the eye and dimensioning the refractive and diffractive parts of the lens such that they together are adapted to compensate at least partly for the refractive error of the eye.

28. A method according to claim 19, comprising providing the refractive part with an aspheric surface, which is adapted to compensate a passing wavefront at least partly for the spherical aberration introduced by at least one optical part of the eye and optionally also by the diffractive part of the lens.

29. A method according to claim 19, comprising providing the refractive part with an aspheric surface, which is adapted to compensate at least partly for spherical aberration as expressed by the 11th normalized Zernike term.

30. A method according to claim 19, comprising providing the lens with a diffractive surface profile.

31. A method according to claim 30, comprising providing the diffractive surface profile with a number of concentric rings.

32. A method according to claim 31, comprising providing the diffractive surface profile with a profile height that equals an integer number of the design wavelength.

33. A method according to claim 19, comprising providing an anterior surface of the lens with an aspheric refractive lens and superimposing a diffractive profile on the aspheric refractive lens.

34. An ophthalmic lens according to claim 11, wherein the lens comprises an anterior surface, and the anterior surface is an aspheric surface, on which a diffractive profile is superimposed.

35. An ophthalmic lens according to claim 13, wherein the lens comprises an anterior surface and a posterior surface, the anterior surface of the lens is an aspheric surface and the posterior surface of the lens is flat and has a diffractive profile.

36. An ophthalmic lens comprising a diffractive part and a refractive part comprising at least one surface, which is configured to compensate a passing wavefront at least partly for at least one type of monochromatic aberration introduced by at least one optical part of the eye, said diffractive part being capable of compensating a passing wavefront at least partly for chromatic aberration introduced by at least one optical part of the eye, said refractive and diffractive parts being adapted together to contribute to a required power of the lens, wherein the refractive part comprises an aspheric surface, which compensates a passing wavefront at least partly for the spherical aberration introduced by at least one optical part of the eye and optionally also by the diffractive part of the lens, and wherein the lens together with the eye provides a polychromatic image quality, which when expressed as MTF(50) (Modulation Transfer Function at 50 cycles per millimeter) is adapted to perform at least about 40% higher than an aspheric lens compensating for the same spherical aberration but without compensating for the chromatic aberration.

37. An ophthalmic lens comprising a diffractive part and a refractive part comprising at least one surface, which is configured to compensate a passing wavefront at least partly for at least one type of monochromatic aberration introduced by at least one optical part of the eye, said diffractive part being capable of compensating a passing wavefront at least partly for chromatic aberration introduced by at least one optical part of the eye, said refractive and diffractive parts being adapted together to contribute to a required power of the lens, wherein the lens comprises an anterior surface, and the anterior surface is an aspheric surface, on which a diffractive profile is superimposed, wherein the diffractive surface profile consists of a number of concentric rings, wherein the profile height of the diffractive surface profile is one design wavelength, and wherein the radial width of a first zone of the diffractive profile is 0.365 mm for a 20D lens.

38. An ophthalmic lens comprising a diffractive part and a refractive part comprising at least one surface, which is configured to compensate a passing wavefront at least partly for at least one type of monochromatic aberration introduced by at least one optical part of the eye, said diffractive part being capable of compensating a passing wavefront at least partly for chromatic aberration introduced by at least one optical part of the eye, said refractive and diffractive parts being adapted together to contribute to a required power of the lens, wherein the lens comprises an anterior surface and a posterior surface, the anterior surface of the lens is an aspheric surface and the posterior surface of the lens is flat and has a diffractive profile, wherein the diffractive part is a diffractive surface profile consisting of a number of concentric rings, and wherein the radial width of a first zone of the diffractive profile is 0.516 mm for a 20D lens.

39. A method of designing an ophthalmic lens according to claim 1, comprising the steps of:
  i) selecting an eye model with a refractive aspheric ophthalmic lens of a predetermined refractive power and a predetermined amount of at least one monochromatic aberration;
  ii) estimating the power of said eye model at different wavelengths, so as to determine the chromatic aberration of the eye model;
  iii) estimating a correction function of how the power varies with the wavelength to be an ideal compensation for said chromatic aberration of the eye model;
  iv) finding a linear function of how power varies with the wavelength, which suitably approximates said correction function;
  v) calculating a provisional zone width of a diffractive profile corresponding to the linear function and calculating the diffractive power of the diffractive profile;
  vi) reducing the refractive power of the refractive ophthalmic lens by the amount of power calculated for the diffractive profile;
  vii) estimating a new correction function of step iii), finding a new linear function of step iv) and calculating a new provisional zone width and a new diffractive power for a new diffractive profile corresponding to the new linear function;
  viii) adjusting the refractive power of the refractive ophthalmic lens such that the total power of a hybrid lens, which comprises both the refractive ophthalmic lens and the diffractive profile and which is adapted to replace the refractive ophthalmic lens in the eye model, equals the predetermined power; and
  ix) repeating steps vii) to viii) until a suitable combination of a refractive part and a diffractive part of the hybrid ophthalmic lens is found that is adapted to provide the eye model with a predetermined power and with a suitable reduction in chromatic aberration.

40. A method according to claim 39, further comprising as a last step measuring the monochromatic aberration of the combination of the eye and the resulting hybrid ophthalmic lens and correcting the refractive part of the ophthalmic lens according to the measurements such that the monochromatic aberration is reduced sufficiently for the combination of eye and ophthalmic lens.

41. A method according to claim 39, wherein the at least one monochromatic aberration of the refractive ophthalmic lens is spherical aberration.

42. A method according to claim 39, wherein the eye model used is the eye model of Navarro (1985).

43. A method according to claim 39, wherein the profile height of the diffractive profile equals an integer number of the design wavelength.

* * * * *